United States Patent [19]

Holub et al.

[11] 3,995,157

[45] Nov. 30, 1976

[54] SURFACE FLAW DETECTION

[75] Inventors: Fred F. Holub, Schenectady, N.Y.; Gerald J. Kennedy, Loveland; Warren F. Weinstein, Fairfield, both of Ohio

[73] Assignee: General Electric Company, Schenectady, N.Y.

[22] Filed: Feb. 18, 1975

[21] Appl. No.: 550,359

[52] U.S. Cl. ............................ 250/302; 252/301.19
[51] Int. Cl.² ........................................ G09K 3/00
[58] Field of Search .............. 250/302; 252/301.2 P, 252/301.2 R

[56] References Cited
UNITED STATES PATENTS

| | | | |
|---|---|---|---|
| 3,546,127 | 12/1970 | Fijalkowski | 250/302 |
| 3,723,449 | 3/1973 | Wirth | 252/301.2 R |
| 3,838,160 | 9/1974 | Molina | 252/301.2 P |

FOREIGN PATENTS OR APPLICATIONS

| | | | |
|---|---|---|---|
| 816,750 | 7/1959 | United Kingdom | 250/302 |

Primary Examiner—Harold A. Dixon
Attorney, Agent, or Firm—John F. McDevitt; Lawrence R. Kempton; Frank L. Neuhauser

[57] ABSTRACT

Flaws in the surface of a physical object, such as cracks, breaks, and other physical discontinuities in metal surfaces are detected by inspection under ultraviolet irradiation after the surface has been coated with a novel flaw detection medium comprising an organic liquid solution of particular organic phosphor materials with an organic binder. The soluble organic phosphor materials found useful in this manner exhibit luminescence when excited by ultraviolet irradiation and are selected from the general class of heterocyclic aromatic nitrogen compounds. In the present inspection method, a coating of the flaw detection medium is applied to the surface being inspected and the dried coating then removed except at the flaw sites prior to inspection. The present liquid flaw detection medium can also be prepackaged for convenient dispensing from a pressurized container through use of conventional propellants such as fluorinated hydrocarbons or their equivalent.

2 Claims, 1 Drawing Figure

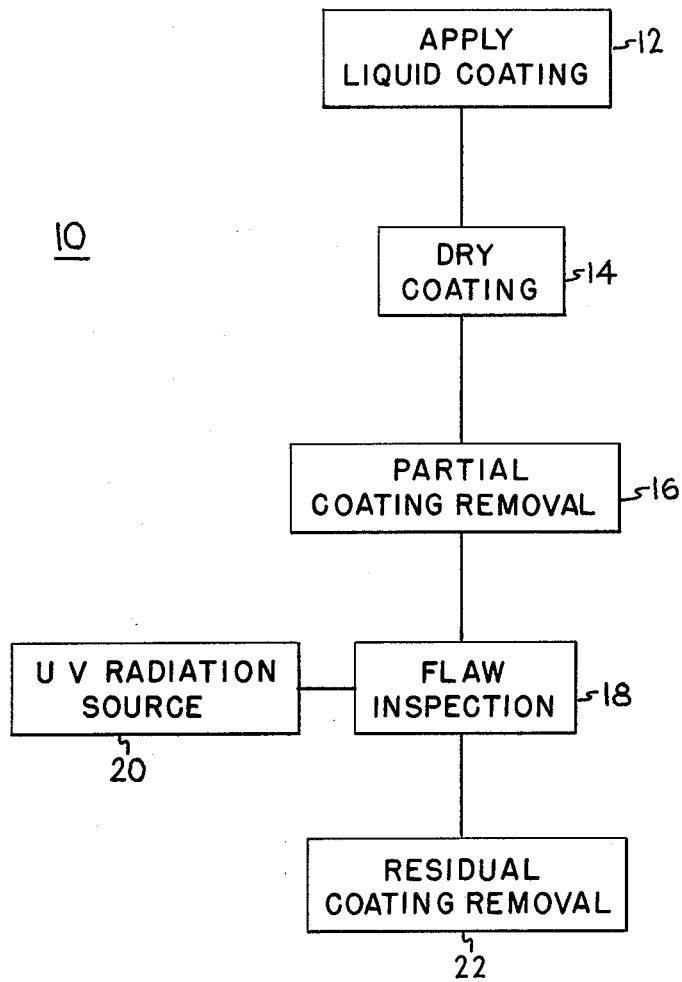

SURFACE FLAW DETECTION

BACKGROUND OF THE INVENTION

The invention herein described was made in the course of or under a contract, or a subcontract thereunder, with the United States Department of the Air force.

In a well-known conventional method of surface flaw detection, wherein the inspection is conducted under ultraviolet irradiation, the medium employed is an organic liquid dispersion of phosphor material with an organic binder. The phosphor material is not dissolved, but simply suspended in the liquid vehicle which has led to less than satisfactory detection when the surface flaws on the physical object being examined are minute. The method of flaw detection with said medium has been to coat the surface being inspected with the organic liquid dispersion, dry the coating, remove the dried coating from the surface except at the flaw sites, and visually examine the treated surface while being exposed to a source of ultraviolet radiation. For convenience in dispensing the conventional liquid medium, it has been packaged in a pressurized metal can having dispenser value means from which the dispersion was sprayed with the assistance of conventional fluorinated hydrocarbon propellants.

The inspection of critical parts, such as, turbine blading which is desirably conducted before as well as after installation in the turbine apparatus requires a flaw detection medium demonstrating high optical resolution capability for minute surface imperfections to be detected. Crack propogation is very rapid upon heating under mechanical stress so that it becomes necessary to identify any imperfections beforehand which could lead to catastrophic failure of the turbine during operation. The conventional surface flaw detection medium lacks sufficient optical resolution to identify minute imperfections reliably because the suspended phosphor particulates do not penetrate the defect cavities. Another problem encountered with use of the conventional surface flaw detection medium is inadequate removal of the dried surface coating to reduce background illumination when the treated surface is examined. The conventional method washes the surface with an organic liquid solution containing a detergent to dissolve the organic binder which adhesively bonds the phosphor particulates to the surface at the flaw sites. Resuspension of the phosphor particulates in the liquid washing medium permits their subsequent removal upon draining or rinsing, and the like. The conventional washing technique has proven inadequate to accomplish this objective due to premature drying of the organic liquid solvent. An improved inspection method not subject to these drawbacks would be desirable especially for critical inspections.

SUMMARY OF THE INVENTION

A novel surface flaw detection system has been discovered which employs a particular class of soluble organic phosphor materials to achieve greater penetration of minute surface discontinuities and provide an effective luminous response from these defect sites. The present liquid detection medium can also contain conventional amounts of a plasticizer for the organic binder to retard the drying time as well as reduce the thickness of the dried coating obtained therefrom. Modification of the dry coating characteristics in this manner facilitates subsequent partial removal of said coating from the surface being inspected and insures a more uniform coverage of the surface before the organic liquid solvent has evaporated. Addition of a plasticizer to the liquid washing medium which can be employed for partial removal of the dry coating also retards evaporation of the organic liquid solvent for a more complete removal of the dry coating.

Generally, the present method of surface flaw detection comprises coating the surface being inspected with an organic liquid solution containing the organic phosphor material and an organic binder, drying the surface coating, removing the surface coating except that portion penetrating the surface flaws, and inspecting the treated surface while being exposed to a source of ultraviolet radiation. Partial removal of the dry surface coating is accomplished in a preferred embodiment by dissolving the material with an organic liquid solvent which further contain conventional amounts of a plasticizer for the organic binder as a drying retardant. The redissolved organic binder and organic luminescent compound are thereby retained longer in liquid suspension for a subsequent removal from the surface by draining, rinsing, and the like.

In conducting the inspection step after the dry coating has been partially removed, an energy source of ultraviolet radiation is employed in the detection system which is preferably devoid of significant visible illumination. Visible illumination can interfere with optical detection of the flaws when reflected from the treated surface. The inspection step can also be conducted utilizing a radiation source which is equipped with fiberoptics to permit inspection of remote surfaces such as already installed turbine blading in an aircraft jet engine or stationary turbine apparatus without requiring that the blading be removed. For example, a commercial borescope type instrument found useful in the present detection system is manufactured by the American Optical Company as Model AA-86683 and provides a radiation source generating principally 3650 Angstrom wavelength radiation combined with fiberoptics.

Useful organic phosphor materials for carrying out the present flaw detection method are particular heterocyclic aromatic nitrogen compounds which are readily soluble in an organic liquid solvent and sufficiently excitable by UV radiation to produce efficient visible luminescence. The useful organic phosphors are further compatible with various thermoplastic polymers commonly employed as adhesive binders and can be selected from the more narrow class of hydroxyphenylbenzazoles and their derivatives, hydroxyphenylbenzothiazoles and their derivatives, benzazolylhydroquinones and their derivatives, pyridinols and pyrimidinols. Particularly useful benzazolylhydroquinones and their derivatives are described in U.S. Pat. No. 3,673,202, issued June 27, 1972 to Charles M. Orlando et al, and assigned to the assignee of the present invention. These compounds emit from the visible and near infrared regions of the spectrum depending upon the particular derivative composition when exposed to ultraviolet light to provide a variety of colors in the present flaw detection system. Particularly useful hydroxyphenylbenzothiazoles and their derivatives are described in U.S. Pat. No. 3,723,449, issued Mar. 27, 1973 to Joseph G. Wirth et al, and assigned to the assignee of the present invention. These compounds emit a yellow-green coloration when employed in the present detection system. Particularly useful pyridinol compounds are described in U.S. Pat. No. 3,676,448, issued July 11, 1972 to Joseph G. Wirth and U.S. Pat. No. 3,767,652, also issued to Joseph G. Wirth, and both assigned to the assignee of the present invention. These compounds produced various colors when excited by ultraviolet radiation dependent upon the particular substituents on the pyridine ring. Particularly useful pyrimidinols demonstrating the requisite solubility and luminescence in the present flaw detection system are described in U.S. Pat. No. 3,658,817, issued Apr. 25, 1972 to Charles M. Orlando and assigned to the assignee of the present invention. These compounds may be characterized as crystalline solid dimers which emit yellow luminescence under ultraviolet irradiation.

Various thermoplastic organic polymers found useful for admixture to provide the present liquid flaw detection medium can be selected from the general class of organic liquid soluble resins which produce a film when dried and are well-known to those skilled in the art as including both homopolymers and copolymers. A particularly useful butyl-isobutylmethacrylate copolymer which is essentially colorless so as not to obscure the desired luminescence can be dissolved in an organic solvent such as methyl ethyl ketone in conventional amounts as a binder. Said solution further contains small amounts from about 2% or less by weight in said solution of the organic phosphor material to provide a suitable liquid detection medium for application of the surface coating. Other useful binder materials include cellulose polymers, other acrylates, such as polymethylmethacrylates and polymethacrylates, polycarbonates and styrene polymers.

Suitable plasticizers for incorporation into the present liquid flaw detection medium are selected from the general class of known plasticizers for the particular polymer binder being employed. For example, diocrylphthlate and triphenylphosphate provide useful plasticizers for the aforementioned methacrylate copolymer found to be a particularly compatible binder with the present organic phosphor materials. Conventional small amounts of these plasticizers maintain sufficient tackiness in the polymer binder after the dry coating has been formed to enable its resolublization with an organic liquid wash or rinse for subsequent removal prior to the inspection step. Such removal of the dry surface coating is further enhanced by incorporating plasticizer in the organic liquid solvent being employed.

BRIEF DESCRIPTION OF THE DRAWING

The accompanying drawing represents a flow chart illustrating the specific steps carried out in accordance with the present detection method along with specialized equipment for the present detection system.

DESCRIPTION OF THE PREFERRED EMBODIMENTS

Referring now to the accompanying drawing, in the preferred embodiment being illustrated for carrying out the present detection method upon already installed turbine blading in an aircraft jet engine, there is shown a particular sequence of progress steps and equipment to provide this inspection. It can be seen from the drawing that the only specialized equipment needed in the detection system 10 is a UV radiation source permitting remote inspection. Accordingly, conventional application means 12 are provided to deposit the present liquid detection medium as a coating on the surface of the turbineblades. This can be accomplished using a manual spray bottle equipped with an extension tube leading to blade location while the engine turbine rotor is being rotated during the coating process. The liquid coating could also be applied from a conventional pressurized metal spray can having dispersing valve means and wherein the liquid detection medium contains a fluorinated hydrocarbon propellant or a comparable equivalent along with a corrosion inhibitor. The applied coating is air dried by continued engine rotation and which could be hastened by use of auxillary drying means 14 such as heating, air circulation and the like. The air dried coating is partially removed in the preferred embodiment with a liquid wash or rinse 16 which is supplied to the coated blade surfaces by liquid nozzles or sprays. Alternately, the applied liquid coating can be partially removed to a satisfactory degree with a liquid wash or rinse before the liquid coating has been dried. The inspection means 18 employed to visually observe luminescence at the flaw sites includes an ultraviolet radiation source 20 in the form of the borescope instrument having an ultraviolet transmitting glass fiberoptic bundle as previously described. In operation, the American Optical Company instrument, Model AA-86683 provides sufficient UV excitation to the blade surfaces being inspected from transmision through the fiberglass optics bundle to permit satisfactory detection of even minute cracks.

While the particular organic phosphor materials found to be useful in the present flaw detection method have been reported as thermally stable, it has been discovered that these materials can be advantageously thermally decomposed to permit complete removal after inspection. More particularly, the residual coating does not produce corrosive intermediates which could enhance further propagation of the surface faults. Consequently, the residual coating material in the surface flaws is removed in the above preferred embodiment after inspection utilizing conventional heating means 22 to heat the already inspected parts. It becomes possible in this manner to sufficiently remove traces of the dried flaw detection medium from the cracks without having to employ additional washing or rinsing of the inspected parts.

The following examples are provided to more fully exemplify carrying out of the present inspection method.

EXAMPLE I

A liquid flaw detection medium was prepared in conventional fashion utilizing 50 milliliters methyl ethyl ketone into which was dissolved 0.8 grams 2-(2-hydroxyphenyl) benzothiazole phosphor and 0.15 grams of a commercial butylisobutylmethacrylate copolymer. To this organic liquid solution was added approximately 0.2 weight percent of triphenylphosphate plasticizer and said admixture was then sprayed upon the surface or turbine blades to be inspected. The liquid coating was air dried by rotating the blading for 3 minutes after which the dry coating was rinsed with 150 millileters of methyl ethyl ketone for its partial removal except at crack locations. The rinsing step was followed by additional air drying action for approximately 6 minutes. Inspection of the treated surface with the borescope equipment previously described resulted in yellow-green emission at the crack locations.

EXAMPLE II

A different liquid flaw detection medium was prepared with 0.8 grams 2-(2-hydroxyphenyl) benzazole phosphor and 0.15 grams of the same methacrylate copolymer employed in the previous example being dissolved in 50 milliliters methyl ethyl ketone. The liquid coating was applied, then dried, and subsequently partially removed all as described in Example I. Inspection of the treated surface under UV radiation produced blue emission at the crack locations.

It will be apparent from the foregoing description that various modifications may be made in the above representative preferred embodiments without departing from the true spirit and scope of the present invention. For example, it is not essential that the dry coating be partially removed from the inspected surface all in a single step since an inspection can be carried out in multiple stages wherein only a particular area is subject to inspection at a given time. Likewise, the liquid coating need not be dried before partial removal, nor is it essential that the residual coating be removed after flaw inspection except on critical parts. It is intended to limit the present invention, therefore, only by the scope of the following claims.

What we claim and desire to secure by Letters Patent of the United States is:

1. A liquid flaw detection medium which comprises an organic liquid solution containing a mixture of soluble organic polymer binder with a plasticizer for the organic polymer binder and a soluble organic phosphor material in the approximate amount 0.2–2.0% by weight in said organic liquid solution which is selected from the class of 2-(2-hydroxyphenyl) benzothiazole and 2-(2-hydroxyphenyl) benzazole.

2. An improved method of detecting flaws in the surface of a physical object which includes:
    a. coating the surface to be inspected with an organic liquid solution containing a mixture of an organic polymer binder and plasticizer for said binder with a soluble organic phosphor material which is excitable by UV radiation and selected from the class of hydroxyphenylbenzazoles and their derivatives, hydroxyphenylbenzothiazoles and their derivatives, benzazolylhydroquinones and their derivatives, pyridinols, and pyrimidinols,
    b. partially removing the surface coating except that portion residing in the surface flaws with an organic liquid solvent containing a plasticizer for the organic binder, and
    c. inspecting the remaining coating while being exposed to a source of UV radiation.

* * * * *